(12) United States Patent
Yao et al.

(10) Patent No.: US 9,775,584 B2
(45) Date of Patent: Oct. 3, 2017

(54) ULTRASOUND PROBE AND ULTRASOUND DIAGNOSIS APPARATUS

(71) Applicant: Toshiba Medical Systems Corporation, Otawara-shi (JP)

(72) Inventors: Cong Yao, Otawara (JP); Naohisa Kamiyama, Utsunomiya (JP); Tatsuro Baba, Otawara (JP); Tetsuya Yoshida, Bergschenhoek (NL)

(73) Assignee: Toshiba Medical Systems Corporation, Otawara-shi (JP)

( * ) Notice: Subject to any disclaimer, the term of this patent is extended or adjusted under 35 U.S.C. 154(b) by 802 days.

(21) Appl. No.: 14/168,490

(22) Filed: Jan. 30, 2014

(65) Prior Publication Data

US 2014/0148701 A1    May 29, 2014

Related U.S. Application Data

(63) Continuation of application No. PCT/JP2012/069900, filed on Aug. 3, 2012.

(30) Foreign Application Priority Data

Aug. 3, 2011    (JP) ................................. 2011-170397
Aug. 2, 2012    (JP) ................................. 2012-172267

(51) Int. Cl.
*A61B 8/00*    (2006.01)
*A61B 8/14*    (2006.01)
*A61B 8/08*    (2006.01)

(52) U.S. Cl.
CPC .............. *A61B 8/4461* (2013.01); *A61B 8/14* (2013.01); *A61B 8/42* (2013.01); *A61B 8/4254* (2013.01); *A61B 8/4455* (2013.01); *A61B 8/0841* (2013.01)

(58) Field of Classification Search
CPC ........... A61B 8/0841; A61B 8/14; A61B 8/42; A61B 8/4254; A61B 8/4455; A61B 8/4461
See application file for complete search history.

(56) References Cited

U.S. PATENT DOCUMENTS 4,870,867 A * 10/1989 Shaulov ............... G01N 29/262
                                                     310/334
5,159,931 A * 11/1992 Pini ...................... A61B 5/0456
                                                     128/916

(Continued)

FOREIGN PATENT DOCUMENTS

JP    2-213331 A    8/1990
JP    5-33708 U    6/1993

(Continued)

OTHER PUBLICATIONS

International Search Report issued on Oct. 23, 2012 for PCT/JP2012/069900 filed on Aug. 3, 2012 with English Transaction.

(Continued)

*Primary Examiner* — Katherine Fernandez
(74) *Attorney, Agent, or Firm* — Oblon, McClelland, Maier & Neustadt, L.L.P.

(57) ABSTRACT

In an ultrasound probe according to an embodiment, a first ultrasound transducer array scans a first scanned plane. A second ultrasound transducer array engages with the first ultrasound transducer array, is provided so as to intersect the first ultrasound transducer array, and scans a second scanned plane different from the first scanned plane. A probe main body is provided with the first ultrasound transducer array and the second ultrasound transducer array, has an opening in a position where the first and the second ultrasound transducer arrays intersect each other, and has a through hole extending to the opening. An engaging part that causes the first and the second ultrasound transducer arrays to engage (Continued)

with each other is configured in such a manner that the angle at which the first and the second ultrasound transducer arrays intersect each other is changeable.

16 Claims, 13 Drawing Sheets

(56) References Cited

U.S. PATENT DOCUMENTS

| | | | | |
|---|---|---|---|---|
| 5,460,179 | A | * | 10/1995 | Okunuki ............ G10K 11/355 600/444 |
| 5,967,985 | A | * | 10/1999 | Hayakawa ........... A61B 8/0833 600/440 |
| 6,014,473 | A | * | 1/2000 | Hossack ................ A61B 8/145 348/169 |
| 6,036,646 | A | * | 3/2000 | Barthe .................... A61B 8/00 128/916 |
| 6,261,234 | B1 | | 7/2001 | Lin |
| 2005/0090742 | A1 | | 4/2005 | Mine et al. |
| 2005/0101868 | A1 | | 5/2005 | Ridley et al. |
| 2007/0208255 | A1 | | 9/2007 | Ridley et al. |

FOREIGN PATENT DOCUMENTS

| | | |
|---|---|---|
| JP | 9-154843 A | 8/1997 |
| JP | 2000-201936 A | 7/2000 |
| JP | 2005-323669 A | 11/2005 |
| JP | 2007-510514 A | 4/2007 |
| JP | 2010-227603 A | 10/2010 |

OTHER PUBLICATIONS

International Written Opinion mailed on Oct. 23, 2012 for PCT/JP2012/069900 filed on Aug. 3, 2012.

* cited by examiner

FIG.3
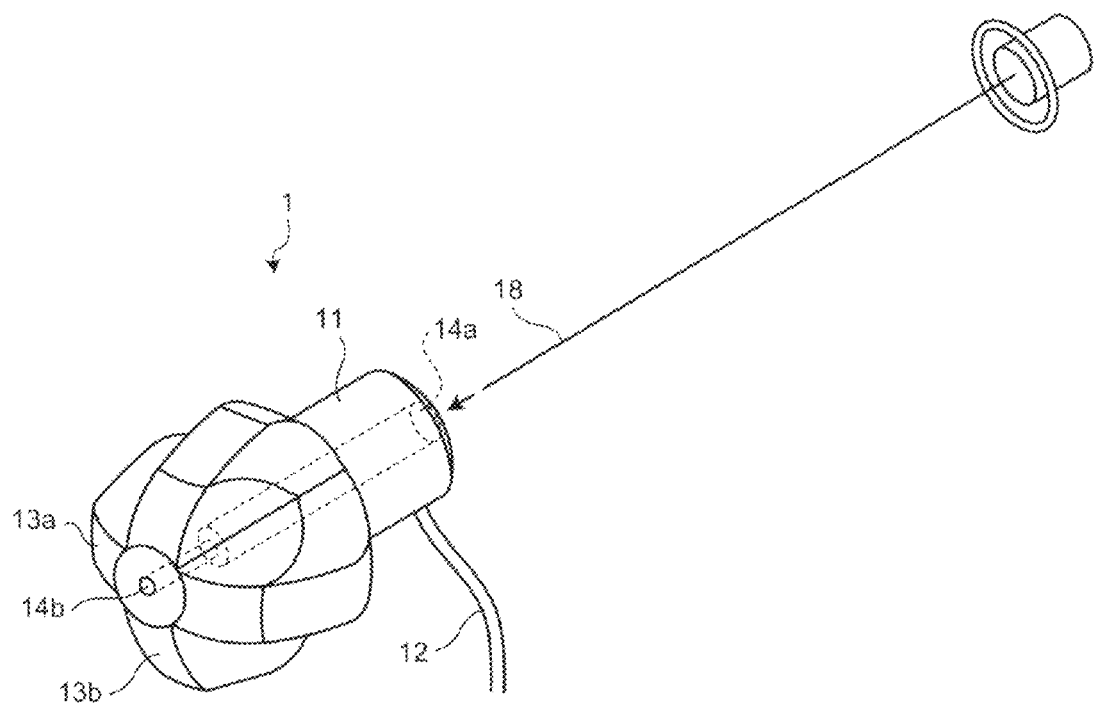
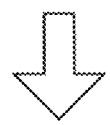
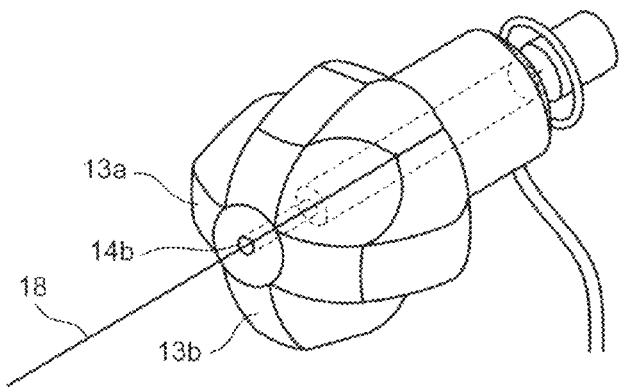

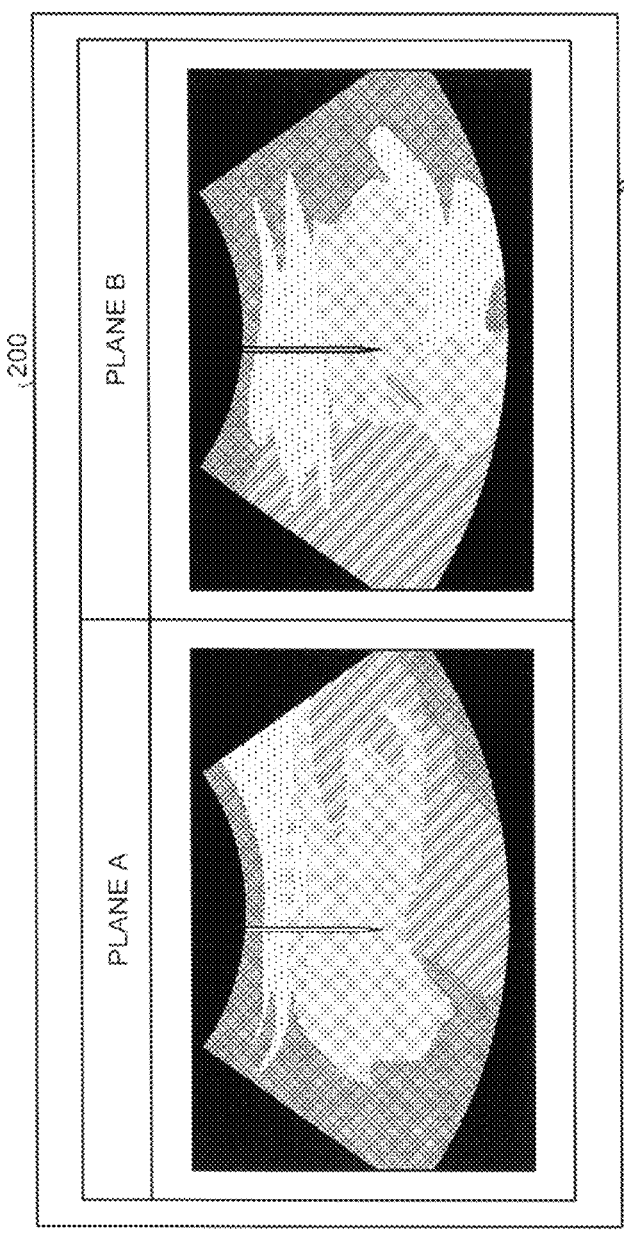
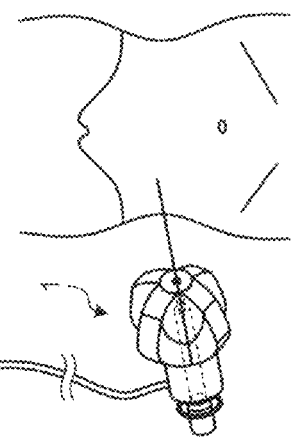
FIG. 4

FIG.5
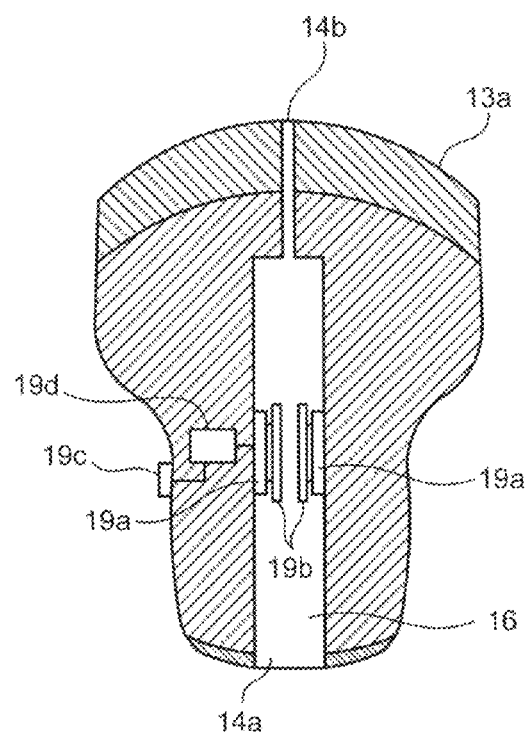
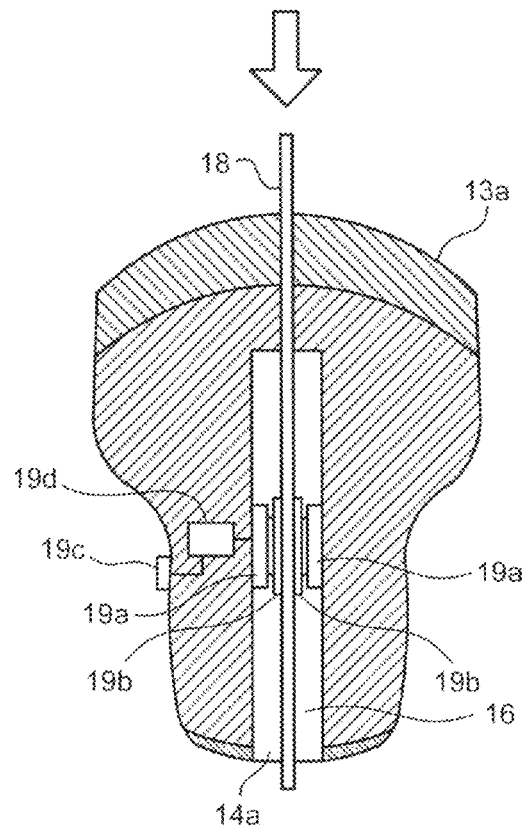

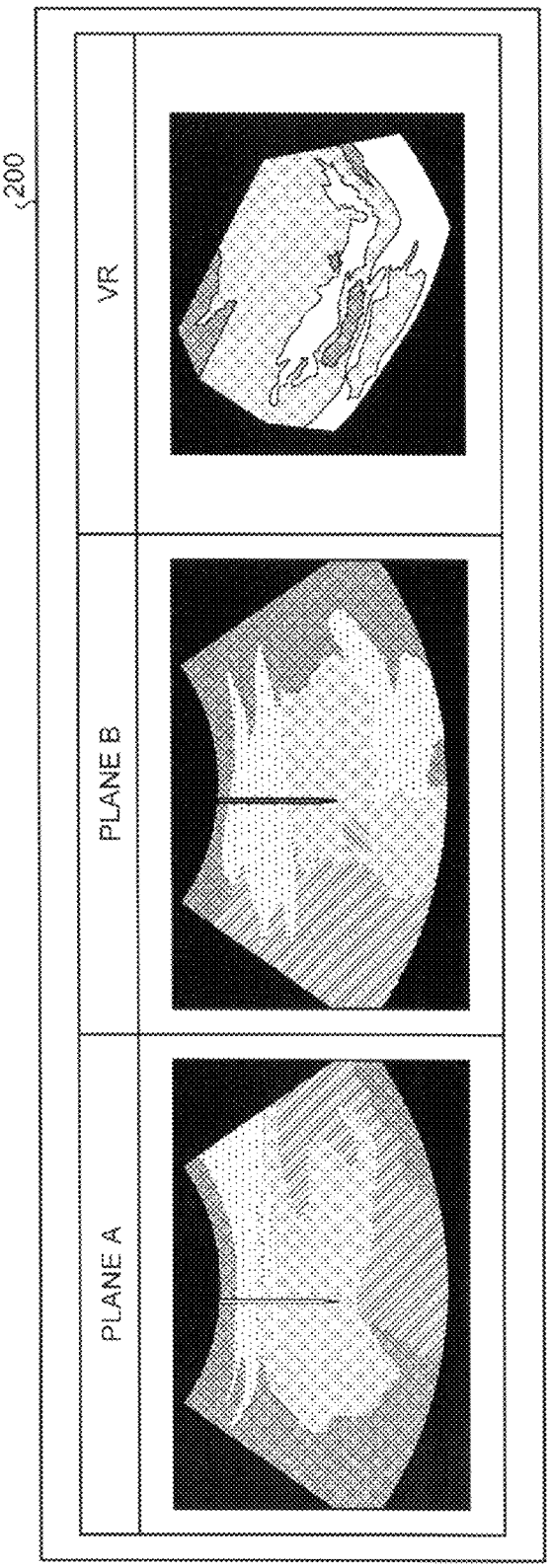

ial Application No. PCT/JP2012/069900, filed on Aug. 3, 2012 which
ULTRASOUND PROBE AND ULTRASOUND DIAGNOSIS APPARATUS

CROSS-REFERENCE TO RELATED APPLICATIONS

This application is a continuation of International Application No. PCT/JP2012/069900, filed on Aug. 3, 2012 which claims the benefit of priority of the prior Japanese Patent Application No. 2011-170397, filed on Aug. 3, 2011, and Japanese Patent Application No. 2012-172267, filed on Aug. 2, 2012, the entire contents of which are incorporated herein by reference.

FIELD

Embodiments described herein relate generally to an ultrasound probe and an ultrasound diagnosis apparatus.

BACKGROUND

Ultrasound diagnosis apparatuses are configured to acquire biological information by emitting an ultrasound pulse generated by a vibration element provided in an ultrasound probe into the inside of a subject and causing the vibration element to receive an ultrasound reflected wave that is generated due to a difference in acoustic impedances among tissues of the subject. Further, with a simple operation of bringing an ultrasound probe into contact with the subject, ultrasound diagnosis apparatuses are capable of displaying ultrasound image data in a real-time manner. Thus, ultrasound diagnosis apparatuses are widely used for making morphological diagnoses and functional diagnoses of various internal organs.

For example, ultrasound diagnosis apparatuses are often used in a puncture process for a biopsy test, a radio frequency ablation (RFA), or the like. To obtain a tissue for a biopsy test, a medical doctor inserts a puncture needle into the body of a subject and extracts the tissue, while viewing a targeted lesion in an ultrasound image in a real-time manner. In another example, to perform an RFA process, a medical doctor inserts an RFA needle up to a site of a lesion while viewing the targeted lesion in an ultrasound image in a real-time manner and subsequently causes the RFA needle to emit a radio frequency wave.

For example, to accurately recognize the puncture needle or the RFA needle during such a manipulation using an ultrasound diagnosis apparatus, an attachment is used for limiting the entering range of the puncture needle, and/or three-dimensional data acquired by employing a two-dimensional (2D) array probe or a mechanical four-dimensional (4D) probe is used for specifying the positions of the puncture needle and the targeted site. According to the conventional technique described above, however, the efficiency of the manipulation involved in a diagnosis and/or a medical treatment may be lowered in some situations.

BRIEF DESCRIPTION OF THE DRAWINGS

FIG. 3 is a drawing of an example in which a puncture needle is installed in the ultrasound probe according to the present embodiment;
FIG. 4 is a drawing of images viewed when a puncture process is performed while using the ultrasound probe according to the present embodiment;
FIG. 5 is a drawing of an example of a vibration mechanism according to the present embodiment;
FIG. 11 is a drawing of exemplary displays of images resulting from a scanning process performed by the ultrasound probe according to the present embodiment.

DETAILED DESCRIPTION

Exemplary Embodiments

According to an embodiment, an ultrasound probe includes a first ultrasound transducer array, a second ultrasound transducer array and a probe main body. The first ultrasound transducer array is used for scanning a first scanned plane. The second ultrasound transducer array that is configured to engage with the first ultrasound transducer array, is provided so as to intersect the first ultrasound transducer array, and is used for scanning a second scanned plane different from the first scanned plane. The probe main body that is provided with the first ultrasound transducer array and the second ultrasound transducer array, has an opening in a position where the first and the second ultrasound transducer arrays intersect each other, and has a through hole extending to the opening. An engaging part that causes the first and the second ultrasound transducer arrays to engage with each other is configured in such a manner that an angle at which the first and the second ultrasound transducer arrays intersect each other is changeable.

Figure 1:
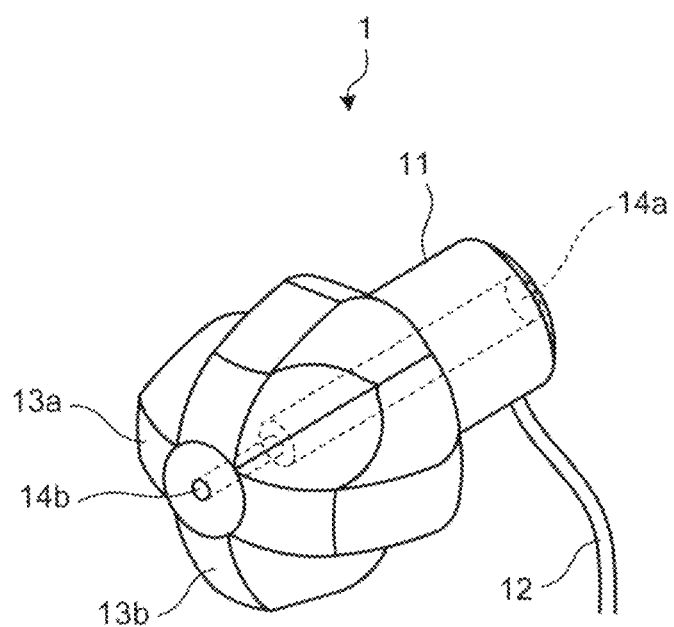
FIG. 1 is a drawing of an exterior appearance of an ultrasound probe according to an embodiment.

An exterior appearance of an ultrasound probe 1 according to an exemplary embodiment will be explained with reference to FIG. 1. FIG. 1 is a drawing of the exterior appearance of the ultrasound probe 1 according to the present embodiment. The ultrasound probe 1 according to the present embodiment includes, as shown in FIG. 1, a probe main body 11 and a cable 12.

The cable 12 sends and receives electric signals between the ultrasound probe 1 and an ultrasound diagnosis apparatus. The probe main body 11 is provided with a first ultrasound transducer array and a second ultrasound transducer array, has an opening in a position where the first and the second ultrasound transducer arrays intersect each other, and has a through hole extending to the opening. For example, as shown in FIG. 1, the probe main body 11 is provided with a first ultrasound transducer array 13a and a second ultrasound transducer array 13b, has an opening 14b in a position where the first and the second ultrasound transducer arrays intersect each other, and has a through hole extending to the opening 14b. In other words, the probe main body 11 has the through hole that extends from an opening 14a to the opening 14b.

The first ultrasound transducer array 13a is configured to scan a first scanned plane. More specifically, the first ultrasound transducer array 13a transduces an electric signal into an ultrasound wave and transmits the ultrasound wave resulting from the transduction to a subject. Further, the first ultrasound transducer array 13a receives a reflected wave and transduces the received ultrasound wave into an electric signal. In this situation, the first ultrasound transducer array 13a is a convex transducer array arranged in a horizontal direction of the ultrasound probe 1 shown in FIG. 1.

The second ultrasound transducer array 13b is provided so as to intersect the first ultrasound transducer array 13a and is configured to scan a second scanned plane different from the first scanned plane. More specifically, the second ultrasound transducer array 13b transduces an electric signal into an ultrasound wave and transmits the ultrasound wave resulting from the transduction to the subject. Further, the second ultrasound transducer array 13b receives a reflected wave and transduces the received ultrasound wave into an electric signal. In this situation, the second ultrasound transducer array 13b is a convex transducer array arranged in a vertical direction of the ultrasound probe 1 shown in FIG. 1. In other words, the ultrasound probe 1 according to the present embodiment is a biplane probe in which the two ultrasound transducer arrays used for scanning the mutually-different scanned planes are arranged.

Figure 2A:
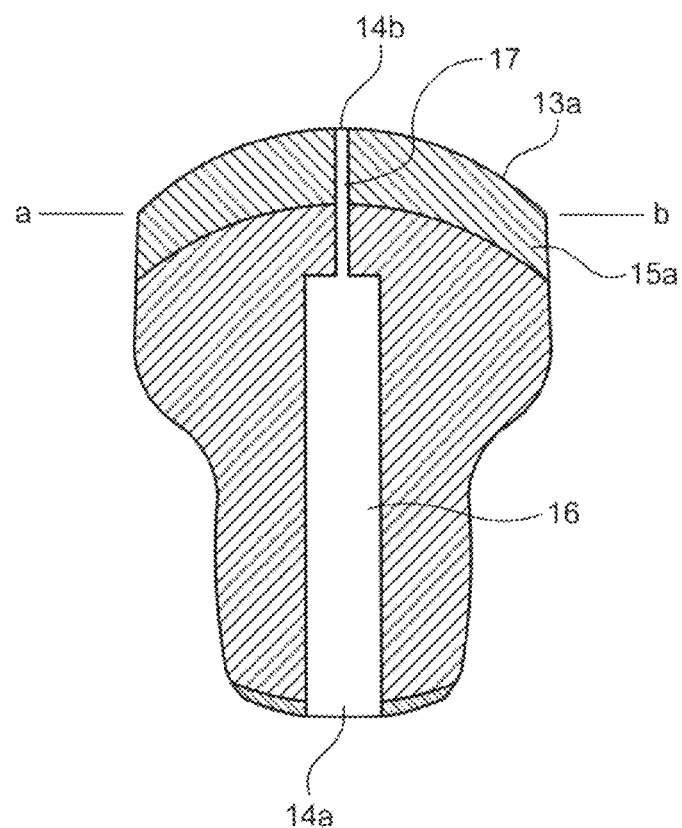
FIG. 2A is a cross-sectional view in a horizontal direction of the ultrasound probe shown in FIG. 1.

In this configuration, the probe main body 11 determines an advancing direction of a medical device that advances out of the opening via the through hole. FIG. 2A is a cross-sectional view in a horizontal direction of the ultrasound probe 1 shown in FIG. 1. As shown in FIG. 2A, the probe main body 11 has a through hole extending from the opening 14a to the opening 14b. The probe main body 11 can have a medical device installed therein by the through hole. More specifically, the probe main body 11 can have a puncture needle, an RFA needle, or the like installed therein.

In this situation, as for the through hole provided in the probe main body 11, a through hole portion 16 positioned on the opening 14a side has a larger diameter, whereas a through hole portion 17 positioned on the opening 14b side has a smaller diameter, as shown in FIG. 2A. The through hole portion 16 is designed to have a larger diameter because a puncture needle, an RFA needle, or the like may be inserted therethrough from the opening 14a, and also, because a vibration device (explained later) may be disposed therein. In contrast, the through hole portion 17 has a diameter that is suitable for the needle inserted from the opening 14a and is configured to limit the advancing direction of the needle by preventing the needle from wobbling in the left-and-right directions. Further, the through hole that goes through a convex transducer array 15a serving as the first ultrasound transducer array 13a corresponds to the through hole portion 17 having the smaller diameter. This arrangement is made so as to reduce the impact of the through hole on the ultrasound waves resulting from scanning processes performed by the convex transducer array 15a.

For example, the convex transducer array 15a includes an acoustic lens, an acoustic matching layer, Flexible Printed Circuits (FPCs), piezoelectric transducer elements, and a rear surface member (a backing member). The acoustic lens converges ultrasound waves. The acoustic matching layer mitigates unconformity of acoustic impedances between the piezoelectric transducer elements and the subject. FPCs send and receive electric signals to and from the piezoelectric transducer elements.

Based on transmission signals supplied from an apparatus main body, the piezoelectric transducer elements generate ultrasound waves, receive reflected waves from the subject, and generate reception signals. The piezoelectric transducer elements are configured with a plurality of piezoelectric transducer element each of which generates an ultrasound wave and generates a reception signal. The rear surface member prevents the ultrasound waves from propagating rearward from the piezoelectric transducer elements.

Figure 2B:
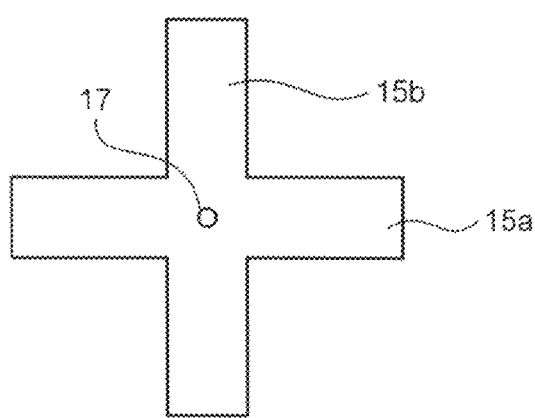
FIG. 2B is a cross-sectional view at a line a-b shown in FIG. 2A.

FIG. 2B is a cross-sectional view at a line a-b shown in FIG. 2A. As shown in FIG. 2B, because the probe main body 11 according to the present embodiment is configured so that the convex transducer arrays 15a and 15b intersect each other and so that the through hole portion 17 is formed therein, it is important to keep the impact of the through hole small.

For example, by arranging the through hole portion 17 so as to have a diameter close to the diameter of a puncture needle, it is possible to keep the impact thereof on the ultrasound transducer arrays small. As for the ultrasound waves that are supposed to be generated in the region where the through hole is formed, the piezoelectric elements positioned in the surroundings thereof are able to complement such ultrasound waves.

FIG. 3 is a drawing of an example in which a puncture needle is installed in the ultrasound probe 1 according to the present embodiment. For example, as shown in FIG. 3, the ultrasound probe 1 according to the present embodiment is configured so that a puncture needle 18 is inserted from the opening 14a and advances out of the opening 14b. In other words, the ultrasound probe 1 according to the present embodiment is configured so that the puncture needle 18 advances while being orthogonal to both the ultrasound transducer array 13a and the ultrasound transducer array 13b.

Next, a problem with the conventional technique will be explained. As mentioned above, according to the conventional technique, to accurately recognize a puncture needle or an RFA needle, an attachment is used for limiting the entering range of the puncture needle, and/or three-dimensional data acquired by employing a 2D array probe or a mechanical 4D probe is used for specifying the positions of the puncture needle and a targeted site.

The attachment is configured to limit the advancing course of the needle in terms of the diameter of a puncture opening for the needle as well as the length, the direction, and the like of the needle, in alignment with a position in a viewed cross section of the probe. As a result, it is possible to have the state of the needle rendered in one cross-sectional image at all times. However, installing the attachment on the probe has an impact on operations of the probe.

Further, the method by which three-dimensional data including a punctured region is obtained by employing a mechanical 4D probe or a 2D array probe on which an attachment is installed and by which the position of the needle is calculated has a problem that can be explained as follows: Although it is possible to specify one cross-sectional image (e.g., on plane A) by installing the attachment, it is still necessary to perform an automatic adjustment or a manual adjustment in order to obtain the other cross-sectional image (e.g., on plane B). When the automatic adjustment or the manual adjustment is performed, the real-time viewing of the advancing course of the needle may experience a delay or a frame rate decrease, depending on the performance capability of the device.

Further, although it is possible to directly obtain plane B from the manual adjustment performed by an operator, the result is dependent on a manipulation performed by the operator. Depending on the positional relationship between the probe and the needle, it is also possible to generate the image of the plane through an interpolation process; however, this method may make the image rough and may make the image quality lower than that of the image of plane A. In addition, the probe and a diagnosis apparatus supporting the probe are expensive, and it is difficult to introduce such a system into general clinics.

Furthermore, during a conventional puncture process, because the puncture needle advances diagonally with respect to the orientation of the ultrasound probe, phenomena such as backscattering may occur depending on the property of the needle, and the image quality of the ultrasound image may be degraded. As explained here, when an operation is performed while the orientation of the probe and the direction of the puncture do not coincide with each other, the operator is required to have a high level of manipulation skill. In some situations, a plurality of operators may collaborate with each other to operate the probe and to perform the puncture process. However, because the timing of the ultrasound probe operation and the timing of the puncture operation need to be coordinated, the operators engaged in such medical activities feel significant physical and mental stress. As explained above, according to the conventional technique, the efficiency of the manipulation involved in a diagnosis and/or a medical treatment may be lowered in some situations.

FIG. 4 is a drawing of images viewed when a puncture process is performed while using the ultrasound probe 1 according to the present embodiment. As shown in FIG. 3, the ultrasound probe 1 according to the present embodiment is configured so that the puncture needle advances while being orthogonal to both the ultrasound transducer array 13*a* and the ultrasound transducer array 13*b*. As a result, when a puncture process is performed by using the ultrasound probe 1 according to the present embodiment, it is possible to have the puncture needle rendered in two images (on plane A and plane B) with certainty, and it is therefore possible to improve the efficiency of the manipulation involved in a diagnosis and/or a medical treatment. The present embodiment is explained by using the example in which the two ultrasound transducer arrays are provided; however, the exemplary embodiments are not limited to this example. It is acceptable to provide an arbitrary number of ultrasound transducer arrays. For example, three or more ultrasound transducer arrays may be provided.

Further, the ultrasound probe 1 according to the present embodiment further includes a vibration mechanism configured to cause the medical device inserted in the through hole to vibrate in directions along the through hole. FIG. 5 is a drawing of an example of the vibration mechanism according to the present embodiment. For example, as shown in FIG. 5, the probe main body 11 includes a vibration device 19*a*, a fixing unit 19*b*, a switch 19*c*, and a controlling unit 19*d*.

Under the control of the controlling unit 19*d* (explained later), the vibration device 19*a* vibrates the fixing unit 19*b* in the directions along the through hole at an arbitrary vibration frequency. The fixing unit 19*b* fixes the medical device and also transfers the vibration generated by the vibration device 19*a* to the medical device. The switch 19*c* is an input device that is operated by the operator and is used for turning on and off the vibration. When the switch is turned on by the operator, the controlling unit 19*d* controls the vibration device 19*a* so as to vibrate at the arbitrary vibration frequency. On the contrary, when the operator turns off the switch, the controlling unit 19*d* controls the vibration device 19*a* so as to stop the vibration.

For example, when the operator turns on the switch while the fixing unit 19*b* is in the state of fixing the puncture needle 18, as shown in the bottom half of FIG. 5, the controlling unit 19*d* causes the vibration device to vibrate at the arbitrary vibration frequency, so that the puncture needle 18 vibrates in the directions along the through hole. For example, by utilizing the vibration function described above when a puncture process is performed on a tissue into which it is difficult for the puncture needle to advance, it is possible to advance the puncture needle up to a targeted site without causing great damage to the tissue. The vibration frequency can arbitrarily be set by the operator. For example, by providing the ultrasound probe 1 with a dial used for setting the vibration frequency in small units, together with the switch 19*c*, the operator is enabled to cause the medical device to vibrate at a desired vibration frequency. The vibration device described above is merely an example. It is acceptable to use any type of vibration mechanism, as long as it is possible to cause the medical device to vibrate in the directions along the through hole.

Figure 6A:
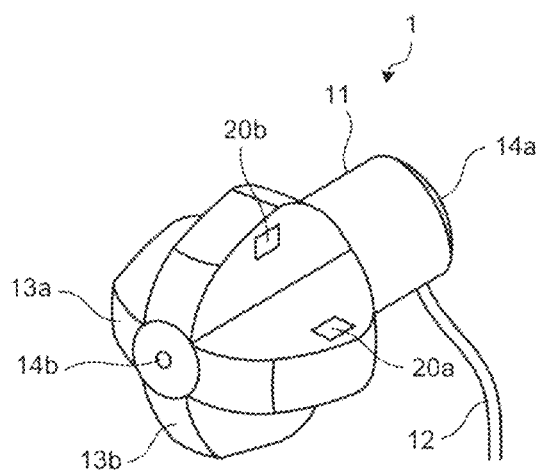
FIG. 6A is a drawing for explaining changing of an angle between ultrasound transducer arrays according to the present embodiment.

Further, the ultrasound probe 1 according to the present embodiment is configured in such a manner that the angle at which the first ultrasound transducer array 13*a* and the second ultrasound transducer array 13*b* intersect each other is changeable. FIG. 6A is a drawing for explaining the changing of the angle between the ultrasound transducer arrays according to the present embodiment. For example, the ultrasound probe 1 is configured so that it is possible to arbitrarily change the angle at which the first ultrasound transducer array 13*a* and the second ultrasound transducer array 13*b* shown in FIG. 6A intersect each other, while using the through hole as an axis.

Figure 6B:
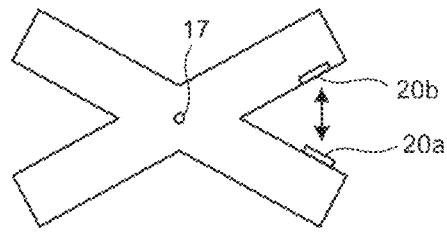
FIG. 6B is a drawing for explaining an angle detection according to the present embodiment.

In this situation, it is also possible to configure the ultrasound probe 1 according to the present embodiment so as to detect the angle at which the first ultrasound transducer array 13*a* and the second ultrasound transducer array 13*b* intersect each other. For example, as shown in FIG. 6A, the probe main body 11 is configured so that the first ultrasound transducer array 13*a* and the second ultrasound transducer array 13*b* include a position sensor 20*a* having a light emitting unit incorporated therein and a receiver 20*b* having a light receiving unit, respectively. FIG. 6B is a drawing for explaining an angle detection according to the present embodiment. In this situation, FIG. 6B is a cross-sectional view orthogonal to the through hole.

For example, as shown in FIG. 6B, by using a position detecting sensor configured so that an infrared ray emitted by the light emitting unit incorporated in the position sensor 20a is received by the receiver 20b, the distance between the first ultrasound transducer array 13a and the second ultrasound transducer array 13b is detected, and further, the angle at which the first ultrasound transducer array 13a and the second ultrasound transducer array 13b intersect each other is detected based on the detected distance. The correspondence relationship between the distance and the angle is set in advance. Further, the position sensor 20a and the receiver 20b are connected to the controlling unit 19d included in the probe main body 11. By performing the process described above, the controlling unit 19d detects the angle at which the first ultrasound transducer array 13a and the second ultrasound transducer array 13b intersect each other.

In the embodiment described above, the example with the position sensor using the infrared ray is explained. However, the exemplary embodiments are not limited to this example. For example, it is acceptable to use a position sensor implementing a magnetic method, an ultrasound method, an optical method, or the like.

In the embodiment described above, the example is explained in which the angle at which the first ultrasound transducer array 13a and the second ultrasound transducer array 13b intersect each other is detected by using the position sensor; however, the exemplary embodiments are not limited to this example. It is acceptable to use any other method as long as it is possible to detect the angle.

Figure 6C:
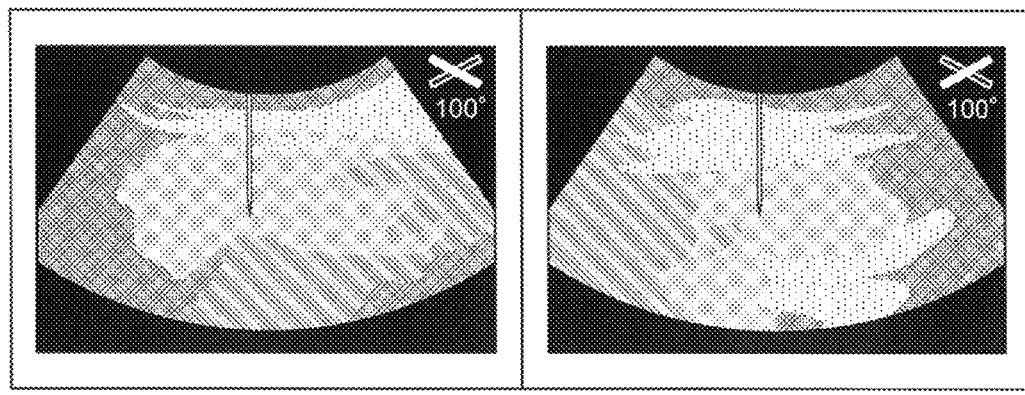
FIG. 6C is a drawing of an example in which angle information is displayed according to the present embodiment.

FIG. 6C is a drawing of an example in which angle information is displayed according to the present embodiment. For example, as shown in FIG. 6C, it is acceptable to arrange the angle detected by the controlling unit 19d so as to be displayed together with an ultrasound image.

Further, the ultrasound probe 1 according to the present embodiment is configured so that medical fluid can flow through the through hole and flow out of the opening 14b. For example, by arranging jelly used in an ultrasound examination or an external-use medicine so as to flow into the ultrasound probe 1 from the opening 14a, the operator is able to arrange the jelly or the external-use medicine to flow out of the ultrasound probe 1 from the opening 14b.

Figure 7:
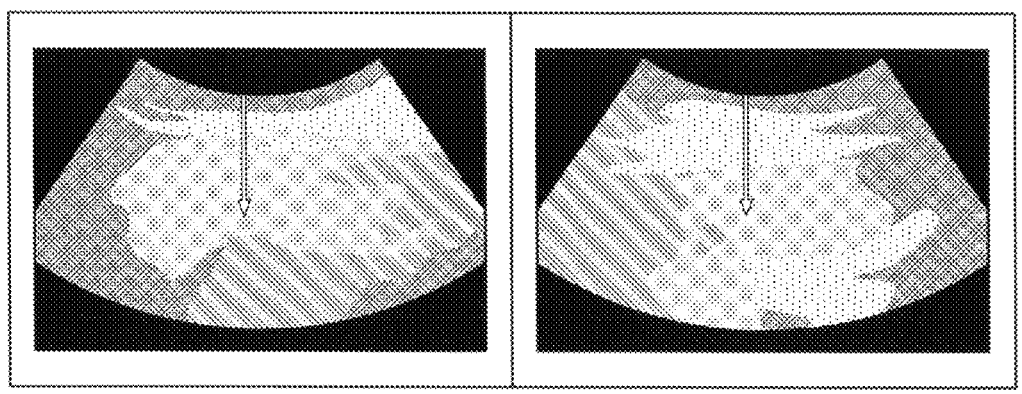
FIG. 7 is a drawing for explaining an exemplary usage of a medical device according to the present embodiment.

Further, it is also possible to insert a physical examination apparatus such as a FibroScan device into the through hole formed in the ultrasound probe 1 according to the present embodiment. FIG. 7 is a drawing for explaining an exemplary usage of a medical device according to the present embodiment. FIG. 7 illustrates a state in which information obtained by a FibroScan device is displayed in an ultrasound image.

For example, as shown in FIG. 7, it is possible to indicate a position in which the FibroScan device has obtained a visceral fat rate, by using an arrow in an ultrasound image. In that situation, it is possible to easily analyze a relationship between characteristics of the ultrasound image and the fat rate.

Further, the ultrasound probe 1 according to the present embodiment is configured so that the first and the second ultrasound transducer arrays are separatable from each other. While being in a separated state, each of the ultrasound transducer arrays functions as an independent ultrasound transducer. More specifically, it is possible to realize the ultrasound probe 1 according to the present embodiment by combining two ultrasound probes each of which functions independently.

Figure 8:
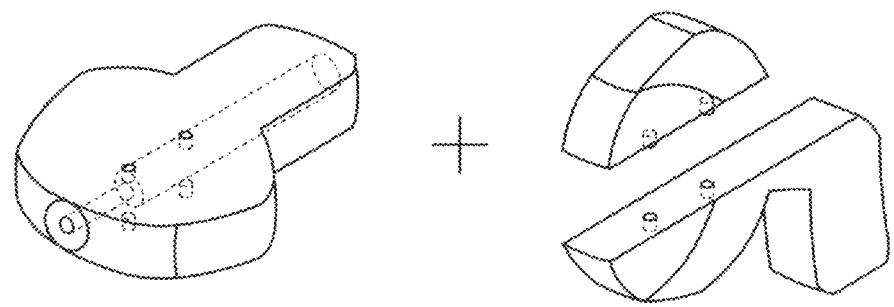
FIG. 8 is a drawing of an example of an assembly-type ultrasound probe according to the present embodiment.

FIG. 8 is a drawing of an example of an assembly-type ultrasound probe according to the present embodiment. FIG. 8 illustrates an example in which two convex ultrasound probes are combined together. For example, as shown in FIG. 8, a through hole is formed in one of the ultrasound probes. Further, the other ultrasound probe is configured, as shown in FIG. 8, so as to be divided into two sections at the center of the probe main body. In this situation, each of the ultrasound probes is provided with a joining part to make it possible to be combined together. In the example shown in FIG. 8, the upper section of the ultrasound probe shown on the right side is joined to the upper surface of the ultrasound probe shown on the left side of FIG. 8, whereas the lower section of the ultrasound probe shown on the right side is joined to the lower surface of the ultrasound probe shown on the left side. As for the ultrasound probe shown on the right side, the upper section and the lower section complement ultrasound waves therebetween when being joined. Further, when the ultrasound probe shown on the right side is used alone, the upper section and the lower section are joined together.

In the embodiment described above, the example is explained in which the two convex ultrasound probes are combined together; however, the exemplary embodiments are not limited to this example. For example, it is acceptable to combine together a convex ultrasound probe and a linear ultrasound probe. Further, it is also acceptable to combine two or more ultrasound probes together.

As another example, it is also acceptable to combine together sector ultrasound probes. In that situation, by configuring the probe so that no piezoelectric transducer elements are provided in the through hole part, it is possible to perform a scanning process more accurately while a focus is placed at a short distance. In other words, in the ultrasound probe configured in this manner, because no ultrasound waves are transmitted from the through hole part (the position near the center of the ultrasound transducer arrays), it is possible to form an acoustic field with only the ultrasound waves from both sides of the ultrasound transducer arrays. When the ultrasound waves transmitted from the transducer elements are considered as spherical waves, it is observed that a spherical wave transmitted from a transducer element positioned directly above the focal point spreads substantially perpendicular to the orientation direction. In contrast, it is observed that a spherical wave transmitted from a transducer element positioned away from the focal point with respect to the orientation direction spreads in a direction diagonal to the focal point. In this situation, to form an acoustic field that is more converged with respect to the orientation direction, it is useful to eliminate the spherical waves that spread perpendicular to the orientation direction. Accordingly, in the configuration where no ultrasound waves are transmitted from the through hole part, it is possible to form a beam having a smaller beam width with respect to the orientation direction than in a configuration where ultrasound waves are transmitted from all the transducer elements. Consequently, with the ultrasound probe configured as described above, it is possible to perform the scanning process more accurately while the focus is placed at the short distance, by controlling the timing with which each of the groups of piezoelectric transducer elements disposed on the two sides of the ultrasound transducer arrays is driven.

Further, with the ultrasound probe configured as described above, even in a situation where a scanning process is performed while a focus is placed at a long distance, it is possible to suppress reception signals from a short-distance acoustic field, which are prone to have noise components. It is therefore possible to, for example, have a puncture needle at a long distance rendered in an image using signals with reduced noise. As explained here, with the ultrasound probe obtained by combining together the sector ultrasound probes, it is possible to perform the short-distance and the long-distance scanning processes more accurately. For example, when a puncture process is performed by using the sector ultrasound probe described above, it is also acceptable to exercise control so as to dynamically vary the depth of the focus by detecting an intrusion depth of the puncture needle.

Figure 9A:
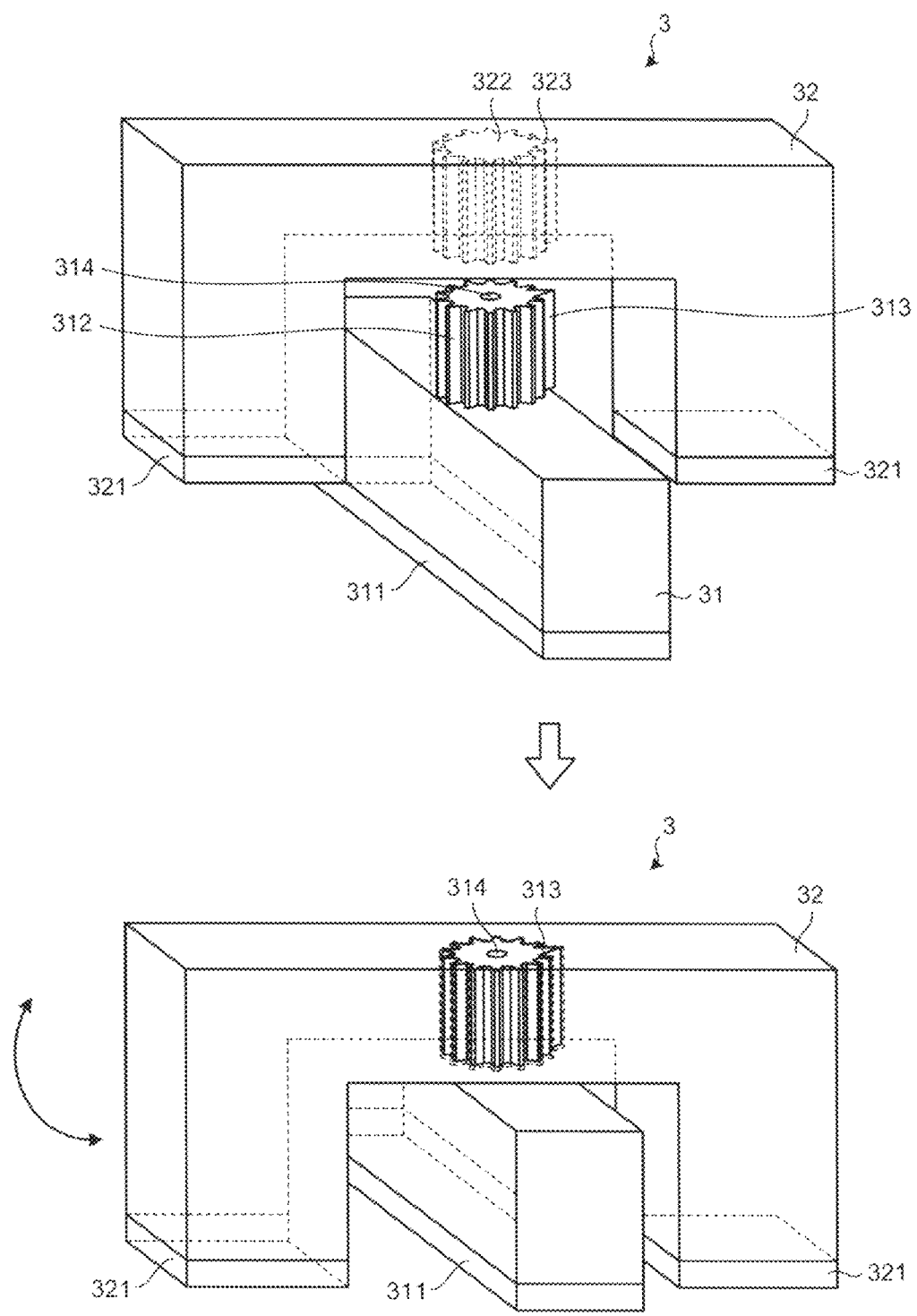
FIG. 9A is a drawing of a modification example of the assembly-type ultrasound probe according to the present embodiment.
Figure 9B:
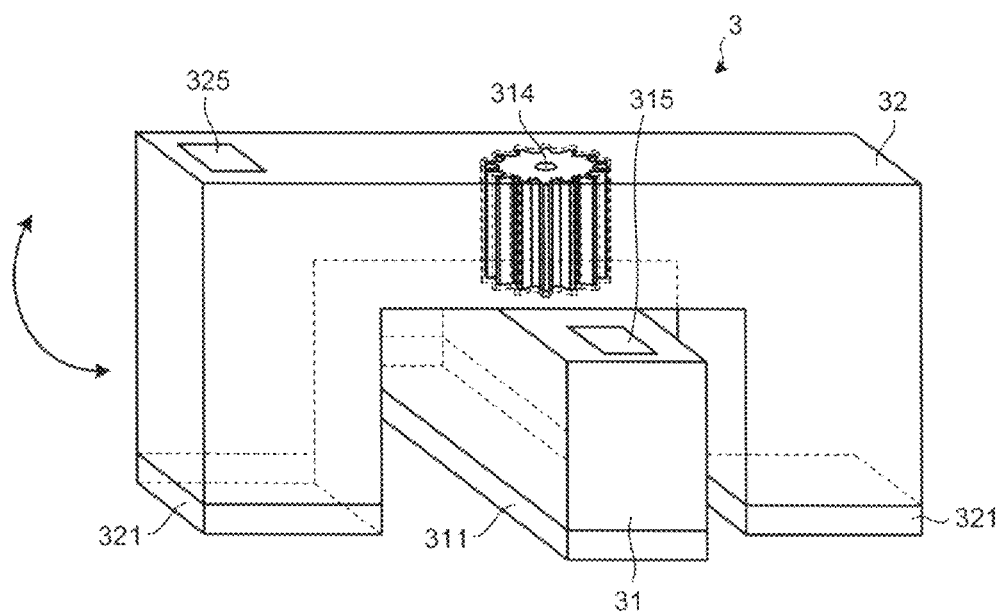
FIG. 9B is a drawing of another modification example of the assembly-type ultrasound probe according to the present embodiment.

Further, in the embodiment described above, the example shown in FIG. 8 is explained as an example of the assembly-type ultrasound probe; however, assembly-type ultrasound probes are not limited to the example shown in FIG. 8. For instance, ultrasound probes shown in FIGS. 9A and 9B are also acceptable. FIGS. 9A and 9B are drawings of modification examples of the assembly-type ultrasound probe according to the present embodiment. In this situation, FIGS. 9A and 9B illustrate assembly-type ultrasound probes each of which is capable of automatically controlling the angle formed by the two ultrasound transducer arrays.

For example, as shown in the top half of FIG. 9A, an ultrasound probe 3 according to a modification example includes a first ultrasound probe 31 and a second ultrasound probe 32. Further, the first ultrasound probe 31 and the second ultrasound probe 32 include a first ultrasound transducer array 311 and a second ultrasound transducer array 321, respectively. In this situation, engaging parts are provided in such a manner that the angle at which the first ultrasound transducer array 311 and the second ultrasound transducer array 321 intersect each other is changeable.

For example, as shown in the top half of FIG. 9A, the engaging parts are configured with a gear-like engaging part with projections 312 and a gear-like engaging part with recesses 322. The engaging part with projections 312 and the engaging part with recesses 322 are disposed on the central axes of the first ultrasound transducer array 311 and the second ultrasound transducer array 321, respectively. Further, as shown in the bottom half of FIG. 9A, the angle at which the first ultrasound transducer array 311 and the second ultrasound transducer array 321 intersect each other is changed as a result of the engaging parts being driven while the gear-like engaging part with projections 312 the gear-like engaging part with recesses 322 are engaged with each other.

For example, the engaging part with projections 312 is disposed on a top part of the first ultrasound probe 31 so as to be able to turn in a circumferential direction and has a motor installed therein. Further, when the motor is controlled by a controlling unit (not shown), the engaging part with projections 312 turns. In this situation, when the engaging part with projections 312 turns while the engaging part with recesses 322 is engaged with the engaging part with projections 312, the second ultrasound probe 32 moves in such a manner that the intersection angle between the second ultrasound probe 32 and the first ultrasound probe 31 changes.

In this situation, for example, as shown in FIG. 9A, the gear-like engaging part with projections 312 and the gear-like engaging part with recesses 322 are provided with an angle detecting projection 313 and an angle detecting recess 323, respectively. For example, as shown in FIG. 9A, the angle detecting recess 323 is positioned so that the tip end is oriented along the lengthwise direction of the second ultrasound probe 32. As a result, when the tip end of the angle detecting projection 313 is oriented along the widthwise direction of the first ultrasound probe 31, it means that the first ultrasound probe 31 and the second ultrasound probe intersect each other at a 90-degree angle.

By detecting the orientation of the tip end of the angle detecting projection 313, the controlling unit (not shown) mentioned above detects the angle at which the first ultrasound probe 31 and the second ultrasound probe intersect each other and thereby performs an angle controlling process. The controlling unit (not shown) that performs the process to control the motor and the angle may be installed in the ultrasound probe 3. Alternatively, the controlling unit may be provided as an independent controlling device or may be provided in an ultrasound diagnosis apparatus. In the section above, the example is explained in which the angle detecting projection 313 and the angle detecting recess 323 are used in the process to control the angle between the first ultrasound probe 31 and the second ultrasound probe; however, the exemplary embodiments are not limited to this example. For instance, another arrangement is acceptable in which a relationship between the number of revolutions of the motor and the angle by which the engaging part with projections 312 turns is calculated in advance, so that the process to control the angle between the first ultrasound probe 31 and the second ultrasound probe is performed by using the number of revolutions of the motor.

Further, it is acceptable to use other various methods to perform the process to control the angle between the first ultrasound probe 31 and the second ultrasound probe. Other modification examples will be explained below, with reference to FIG. 9B. FIG. 9B illustrates an example in which the angle detecting projection 313 and the angle detecting recess 323 are omitted from the ultrasound probe 3 shown in FIG. 9A and in which a position sensor 315 and another position sensor 325 are provided instead. For example, the ultrasound probe 3 shown in FIG. 9B is used in a magnetic field generated by a transmitter (not shown), and the angle between the first ultrasound probe 31 and the second ultrasound probe is detected and controlled based on a positional relationship between the position sensor 315 and the position sensor 325 within the magnetic field. In other words, the ultrasound probe 3 shown in FIG. 9B is configured so that the angle controlling process is performed based on changes in the distance between the position sensor 315 and the position sensor 325. In the examples shown in FIGS. 9A and 9B, the engaging part with projections 312 is provided with a through hole 314. In this situation, the through hole 314 is provided at the center of a shaft that transfers the power of the motor to the engaging part with projections 312.

The angle controlling process performed by using one or more position sensors is not limited to the example described above. For example, it is acceptable to perform an angle controlling process by, as shown in FIGS. 6A and 6B, disposing a position sensor including a light emitting unit and a receiving unit including a light receiving unit on lateral faces of the first ultrasound probe 31 and the second ultrasound probe 32, respectively.

Figure 10A:
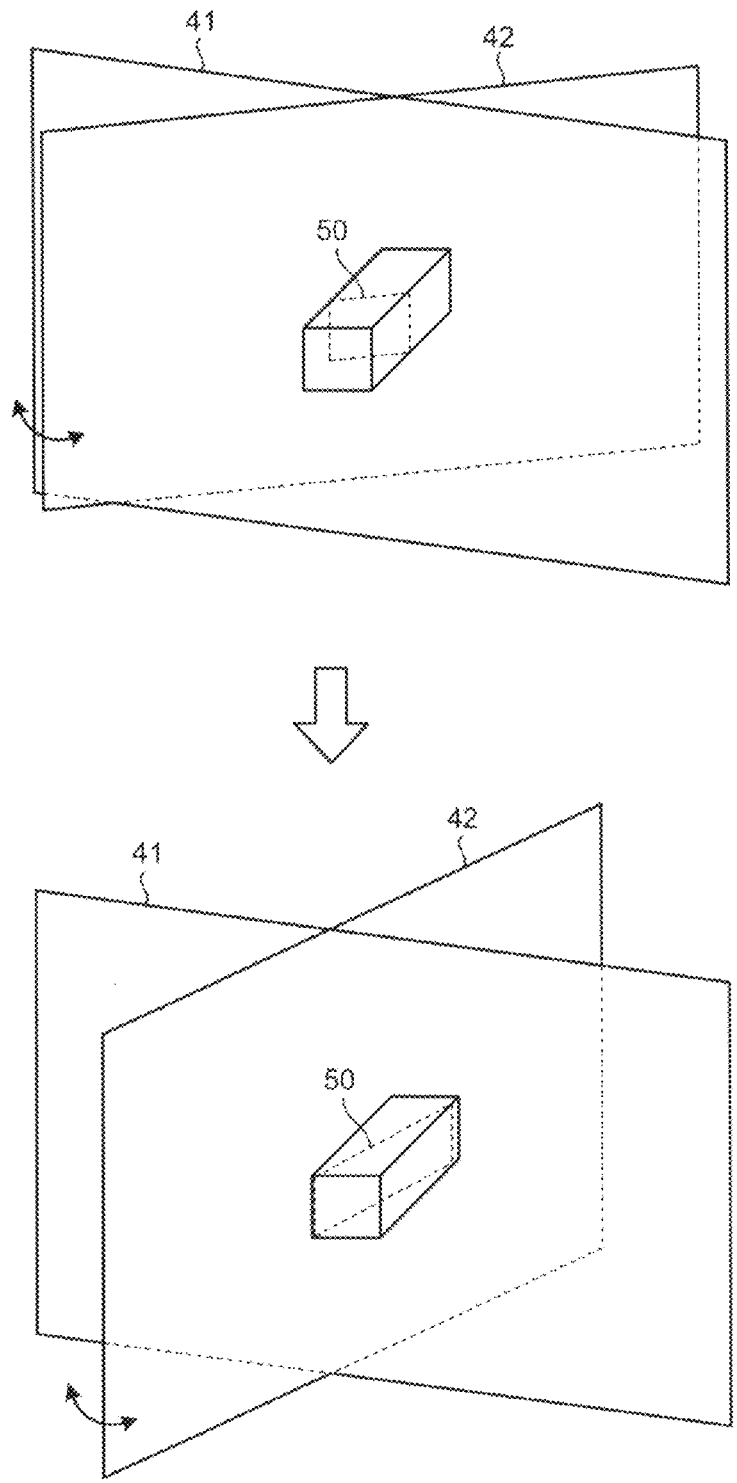
FIG. 10A is a drawing for explaining an example of an angle controlling process performed by the ultrasound probe according to the present embodiment.
Figure 10B:
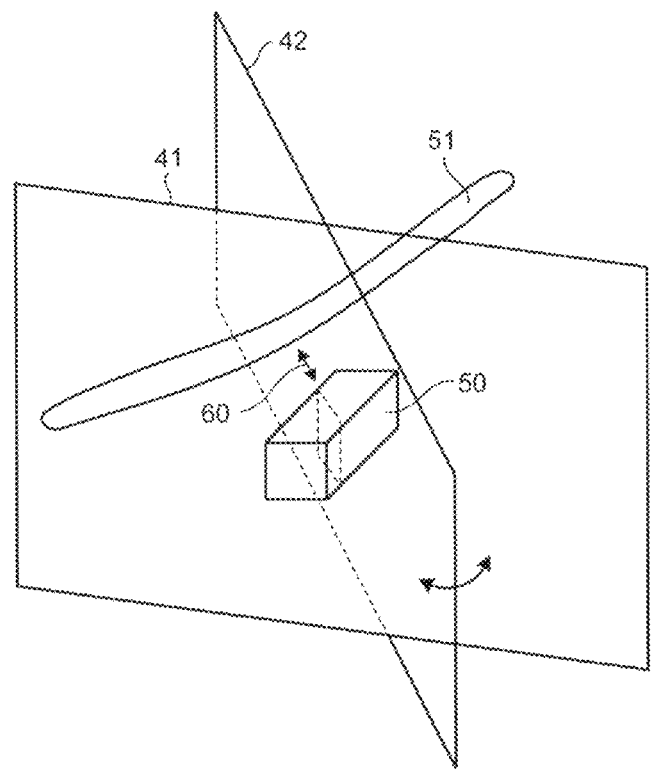
FIG. 10B is a drawing for explaining another example of the angle controlling process performed by the ultrasound probe according to the present embodiment.

In the ultrasound probe according to the present embodiment, the angle controlling process is automatically performed in such a manner that, as described above, the first ultrasound transducer array 311 and the second ultrasound transducer array 321 intersect each other at an arbitrary angle. In this situation, in the ultrasound probe according to the present embodiment, the angle controlling process is performed so as to be able to provide an effective image for performing a puncture process. Examples of the angle controlling process will be explained below, with reference to FIGS. 10A to 10C. FIGS. 10A and 10B are drawings for explaining the examples of the angle controlling process performed by the ultrasound probe according to the present embodiment.

For example, in the ultrasound probe according to the present embodiment, the engaging parts are driven in such a manner that one of the first and the second ultrasound transducer arrays scans such a cross-sectional plane that maximizes the length of a puncture target region. For example, as shown in FIG. 10A, the angle controlling process of the ultrasound probe is performed in such a manner that a scanned cross-sectional plane 42 scanned by the second ultrasound transducer array corresponds to the longest cross-sectional plane of a puncture target region 50. In that situation, for example, the ultrasound probe performs scanning processes while varying, at a predetermined speed, the angle between the first and the second ultrasound transducer arrays. Further, a controlling unit (not shown) extracts such a cross-sectional plane that maximizes the length of the puncture target region 50, from image data resulting from the scanning processes performed at the different angles. The ultrasound probe is controlled so as to be locked at the angle used for scanning the extracted cross-sectional plane.

In another example, in the ultrasound probe according to the present embodiment, the engaging parts are driven in such a manner that one of the first and the second ultrasound transducer arrays scans such a cross-sectional plane that minimizes the distance between a puncture target region and a blood vessel. For example, as shown in FIG. 10B, the angle controlling process of the ultrasound probe is performed in such a manner that the cross-sectional plane 42 scanned by the second ultrasound transducer array corresponds to such a cross-sectional plane that minimizes a distance 60 between the puncture target region 50 and a blood vessel 51. In that situation, for example, the ultrasound probe performs scanning processes while varying, at a predetermined speed, the angle between the first and the second ultrasound transducer arrays. Further, a controlling unit (not shown) extracts such a cross-sectional plane that minimizes the distance between the puncture target region 50 and the blood vessel 51, from image data resulting from the scanning processes performed at the different angles. The ultrasound probe is controlled so as to be locked at the angle used for scanning the extracted cross-sectional plane.

The controlling unit (not shown) mentioned above may be installed in the ultrasound probe. Alternatively, the controlling unit may be provided as an independent controlling device or may be provided in an ultrasound diagnosis apparatus. A plane 41 shown in FIGS. 10A and 10B is a cross-sectional plane scanned by the first ultrasound transducer array.

Figure 10C:
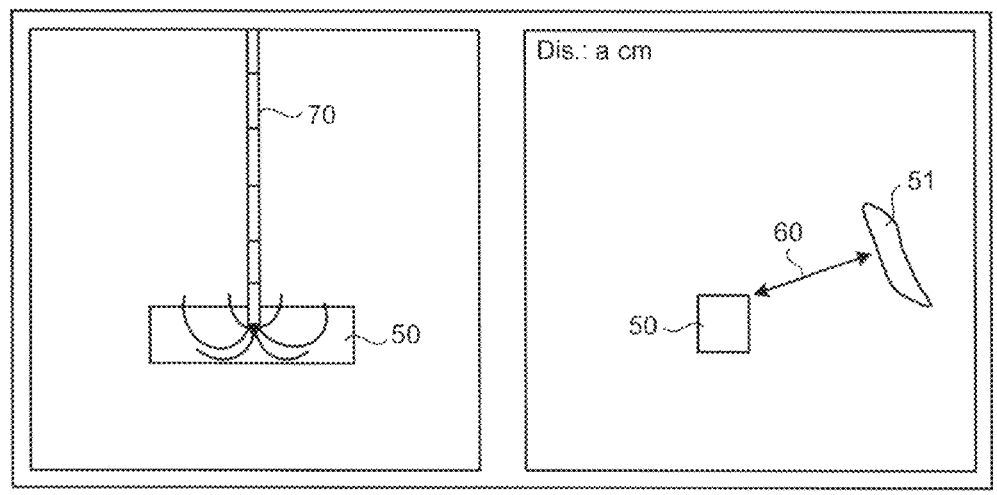
FIG. 10C is a drawing of examples of images obtained when scanning processes are performed at the angles shown in FIGS. 10A and 10B, respectively.

FIG. 10C is a drawing of examples of images obtained when scanning processes are performed at the angles shown in FIGS. 10A and 10B, respectively. An image obtained by performing a scanning process at the angle shown in FIG. 10A is shown on the left side of FIG. 10C, whereas an image obtained by performing a scanning process at the angle shown in FIG. 10B is shown on the right side of FIG. 10C. For example, when the scanning process is performed at the angle shown in FIG. 10A, such a cross-sectional plane that maximizes the length of the puncture target region 50 is displayed, as shown on the left side of FIG. 10C. As a result, when a cauterization treatment is performed by using an RFA needle 70, for example, while the treated site is cauterized radially from the tip end of the RFA needle, it is possible to avoid the situation where some of the target region remains uncauterized. In other words, by cauterizing the puncture target region 50 rendered in the image, it is possible to cauterize the entire region. It is therefore possible to avoid the situation where some of the target region remains uncauterized. The puncture target region 50 may be a region rendered three-dimensionally by the operator or may be a region detected based on differences in brightness values, blood flow rates, bloodstream powers, contrast intensities of the contrast agent, time periods during which the contrast agent stays, or the like.

In another example, when the scanning process is performed at the angle shown in FIG. 10B, such a cross-sectional plane that minimizes the distance 60 between the puncture target region 50 and the blood vessel 51 is displayed, as shown on the right side of FIG. 10C. As a result, when a cauterization treatment is performed, for example, it is possible to prevent the blood vessel from being damaged. Further, for example, when the scanning process is performed at the angle shown in FIG. 10B, it is also acceptable to display the numerical value of the distance 60 simultaneously with the image in a format such as "Dis.: a mm" (where "a" denotes the numerical value calculated based on a measuring result), as shown on the right side of FIG. 10C. With this arrangement, it is possible to further prevent the blood vessel from being damaged during the cauterization process, for example.

As explained above, the ultrasound probe according to the present embodiment is configured so that the scanning processes are performed on the two axes of the first ultrasound transducer array and the second ultrasound transducer array. In other words, the ultrasound probe according to the present embodiment is able to scan a three-dimensional region by receiving, through the first ultrasound transducer array and the second ultrasound transducer array, the reflected-wave signals from the regions positioned between the ultrasound transducer arrays. Further, the ultrasound probe according to the present embodiment is able to change the shape of a focus by changing the intersection angle between the first and the second ultrasound transducer arrays. In other words, the ultrasound probe according to the present embodiment is able to reduce the focus size of the axis having the smaller intersection angle by changing the intersection angle from 90 degrees and to enhance the resolution of the image. By changing the intersection angle, the viewer is able to arbitrarily select, from between the two axes, the side on which the resolution is to be enhanced. In an example, it is possible to perform a scanning process while enhancing the resolution either in the direction in which a blood vessel extends or in the direction in which a tumor extends, which is orthogonal to the direction in which the blood vessel extends.

FIG. 11 is a drawing of exemplary displays of images resulting from a scanning process performed by the ultrasound probe according to the present embodiment. For example, by using the ultrasound probe according to the present embodiment, it is possible to display, on a display unit a Volume Rendering (VR) image, in addition to images on plane A and plane B, as shown in FIG. 11.

Figure 12:
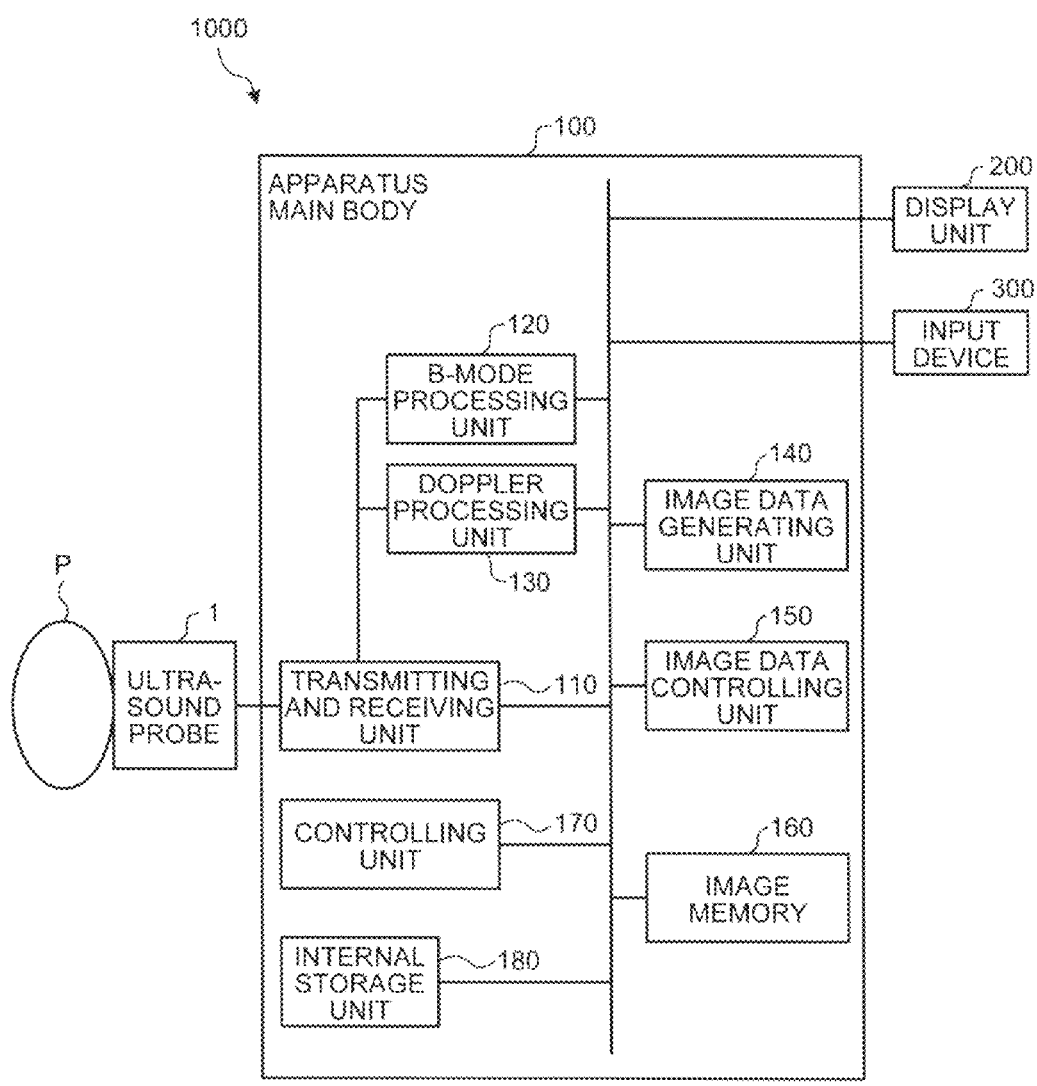
FIG. 12 is a drawing of an example of an overall configuration of an ultrasound diagnosis apparatus according to the present embodiment.

Next, an ultrasound diagnosis apparatus including the ultrasound probe according to the present embodiment will be explained. FIG. 12 is a drawing of an example of an overall configuration of an ultrasound diagnosis apparatus 1000 according to the present embodiment. As shown in FIG. 12, the ultrasound diagnosis apparatus 1000 according to the present embodiment includes the ultrasound probe 1, an input device 300, a display unit 200, and an apparatus main body 100.

The ultrasound probe 1 is the ultrasound probe according to the present embodiment described above. The ultrasound probe 1 includes the plurality of piezoelectric transducer elements, which generate the ultrasound waves based on a drive signal supplied from a transmitting and receiving unit 110 included in the apparatus main body 100 (explained later) and which further receive reflected waves from a subject P and convert the received reflected waves into electric signals. Further, the ultrasound probe 1 includes matching layers included in the piezoelectric transducer elements, as well as the backing member that prevents the ultrasound waves from propagating rearward from the piezoelectric transducer elements.

When an ultrasound wave is transmitted from the ultrasound probe 1 to the subject P, the transmitted ultrasound wave is repeatedly reflected on a surface of discontinuity of acoustic impedances at a tissue in the body of the subject P and is received as a reflected-wave signal by the plurality of piezoelectric transducer elements included in the ultrasound probe 1. The amplitude of the received reflected-wave signal is dependent on the difference between the acoustic impedances on the surface of discontinuity on which the ultrasound wave is reflected. When the transmitted ultrasound pulse is reflected on the surface of a flowing bloodstream or a cardiac wall, the reflected-wave signal is, due to the Doppler Effect, subject to a frequency shift, depending on a velocity component of the moving members with respect to the ultrasound wave transmission direction. The ultrasound probe 1 according to the present embodiment is a one-dimensional ultrasound probe in which the plurality of piezoelectric transducer elements is arranged in a row.

The input device 300 receives various types of setting requests from an operator of the ultrasound diagnosis apparatus 1000 and transfers the received various types of setting requests to the apparatus main body 100. The input device 300 is configured with, for example, a trackball, a switch, a button, a touch command screen, a keyboard, and/or a mouse.

The display unit 200 displays a Graphical User Interface (GUI) used by the operator of the ultrasound diagnosis apparatus 1000 to input the various types of setting requests through the input device 300 and displays ultrasound images generated by the apparatus main body 100.

The apparatus main body 100 is an apparatus configured to generate the ultrasound images based on the reflected waves received by the ultrasound probe 1. As shown in FIG. 12, the apparatus main body 100 includes the transmitting and receiving unit 110, a B-mode processing unit 120, a Doppler processing unit 130, an image data generating unit 140, an image data controlling unit 150, an image memory 160, a controlling unit 170, and an internal storage unit 180.

The transmitting and receiving unit 110 includes a trigger generating circuit, a delaying circuit, a pulser circuit, and the like and is configured to supply the drive signal to the ultrasound probe 1. The pulser circuit repeatedly generates a rate pulse for forming a transmission ultrasound wave, at a predetermined rate frequency. The delaying circuit applies a delay period that is required to converge the ultrasound wave generated by the ultrasound probe 1 into the form of a beam and to determine transmission directionality and that corresponds to each of the piezoelectric transducer elements, to each of the rate pulses generated by the pulser circuit. Further, the trigger generating circuit applies a drive signal (a drive pulse) to the ultrasound probe 1 with timing based on the rate pulses. In other words, the delaying circuit arbitrarily adjusts the directions of the transmissions from the piezoelectric transducer element surfaces, by varying the delay periods applied to the rate pulses.

The transmitting and receiving unit 110 includes an amplifier circuit, an Analog/Digital (A/D) converter, an adder, and the like and generates reflected-wave data by performing various types of processes on the reflected-wave signal received by the ultrasound probe 1. The amplifier circuit amplifies the reflected-wave signal for each of channels and performs a gain correcting process thereon. The A/D converter applies an A/D conversion to the gain-corrected reflected-wave signal and applies a delay period required to determine reception directionality. The adder generates the reflected-wave data by performing an adding process on the reflected-wave signals processed by the A/D converter. As a result of the adding process performed by the adder, reflected components from the direction corresponding to the reception directionality of the reflected-wave signal are emphasized.

In this manner, the transmitting and receiving unit 110 controls the transmission directionality and the reception directionality in the transmission and the reception of the ultrasound wave. The transmitting and receiving unit 110 has a function to be able to instantly change delay information, the transmission frequency, the transmission drive voltage, the number of aperture elements, and the like, under the control of the controlling unit 170 (explained later). In particular, the configuration to change the transmission drive voltage is realized by using a linear-amplifier-type oscillation circuit of which the value can be instantly switched or by using a mechanism configured to electrically switch between a plurality of power source units. Further, the transmitting and receiving unit 110 is also capable of transmitting and receiving mutually-different waveforms in correspondence with different frames or different rates.

The B-mode processing unit 120 receives the reflected-wave data, which is the processed reflected-wave signals on which the gain correction process, the A/D conversion process, and the adding process have been performed, from the transmitting and receiving unit 110 and generates data (B-mode data) in which the strength of each signal is expressed by a degree of brightness, by performing a logarithmic amplification, an envelope detection process, and the like on the received reflected-wave data.

In this situation, the B-mode processing unit 120 is able to change the frequency band to be rendered in an image, by changing the detected frequency. Further, the B-mode processing unit 120 is capable of performing wave-detection processes at two mutually-different wave-detection frequencies in parallel, on one piece of received data.

By using the abovementioned function of the B-mode processing unit 120, it is possible to separate, from one piece of received data for a region of interest in the subject P into whom an ultrasound contrast agent has been injected, reflected-wave data using the ultrasound contrast agent (microbubbles and bubbles) that flows through the region of interest as a source of reflection and reflected-wave data using the tissues that are present in the region of interest as a source of reflection. The image data generating unit 140 (explained later) is therefore possible to generate a contrast image obtained by rendering the flowing bubbles with a high sensitivity and a tissue image obtained by rendering the tissues for observing morphological information.

The Doppler processing unit 130 extracts bloodstreams, tissues, and contrast echo components under the influence of the Doppler effect by performing a frequency analysis so as to obtain velocity information from the reflected-wave data received from the transmitting and receiving unit 110, and further generates data (Doppler data) obtained by extracting moving member information such as an average velocity, the dispersion, the power, and the like for a plurality of points.

The image data generating unit 140 generates ultrasound images that are consecutive in a time sequence, from the B-mode data generated by the B-mode processing unit 120 and the Doppler data generated by the Doppler processing unit 130. Further, the image data generating unit 140 stores the generated ultrasound images into the image memory 160.

The image data controlling unit 150 sequentially obtains, along the time sequence, the ultrasound images generated by the image data generating unit 140. After that, the image data controlling unit 150 sequentially converts the obtained ultrasound images into display-purpose images and stores the images resulting from the conversion into the image memory 160. More specifically, the image data controlling unit 150 generates the display-purpose images (the B-mode images and the Doppler images) by reading the ultrasound images generated by the image data generating unit 140 from the image memory 160 and converting (by performing a scan convert process) the read ultrasound images into a scanning line signal sequence in a video format used by, for example, television. The image data controlling unit 150 then stores the generated display-purpose images into the image memory 160 again. The image data controlling unit 150 also exercises control related to the acquisition of image data. The acquisition of image data performed by the image data controlling unit 150 according to the present embodiment will be explained in detail later.

The image memory 160 stores therein, raw data (the B-mode data and the Doppler data) generated by the B-mode processing unit 120 and the Doppler processing unit 130, as well as the ultrasound images generated by the image data generating unit 140, and the display-purpose images generated by the image data controlling unit 150. Further, the image memory 160 stores therein processing results of the image data controlling unit 150. Further, the image memory 160 stores therein, as necessary, output signals (Radio Frequency (RF)) that are immediately out of the transmitting and receiving unit 110, brightness signals of images, various types of raw data, and the like.

The controlling unit 170 controls the entire processes performed by the ultrasound diagnosis apparatus 1000. More specifically, the controlling unit 170 controls various types of processes performed by the transmitting and receiving unit 110, the B-mode processing unit 120, the Doppler processing unit 130, the image data generating unit 140, and the image data controlling unit 150. For example, based on the various types of setting requests input by the operator via the input device 300, as well as various types of control computer programs and various types of setting information read from the internal storage unit 180, and various types of setting information received from the image data controlling unit 150 (explained later), the controlling unit 170 exercises control over various types of processes and exercises control so that the display unit 200 displays the display-purpose images stored in the image memory 160.

The internal storage unit 180 stores therein various types of data such as a control computer program to realize ultrasound transmissions and receptions, image processing, and display processing, as well as diagnosis information (e.g., patients' IDs, medical doctors' observations) and diagnosis protocols. Further, the internal storage unit 180 may be used, as necessary, for storing therein any of the images stored in the image memory 160.

As explained above, according to the present embodiment, the first ultrasound transducer array 13*a* is configured to scan the first scanned plane. The second ultrasound transducer array 13*b* is provided so as to intersect the first ultrasound transducer array 13*a* and is configured to scan the second scanned plane different from the first scanned plane. Further, the probe main body 11 is provided with the first ultrasound transducer array 13*a* and the second ultrasound transducer array 13*b*, has the opening 14*b* in the position where the first and the second ultrasound transducer arrays intersect each other, and has the through hole extending to the opening 14*b*. Accordingly, the ultrasound probe 1 according to the present embodiment is able to have the medical device rendered in the two or more ultrasound images, with certainty, and makes it possible to improve the efficiency of the manipulation involved in the diagnosis and/or the medical treatment.

Further, according to the present embodiments, the first ultrasound transducer array 311 is configured to scan the first scanned plane. Further, the second ultrasound transducer array 321 is provided so as to engage with the first ultrasound transducer array 311 and so as to intersect the first ultrasound transducer array 311 and is configured to scan the second scanned plane different from the first scanned plane. Further, the probe main body 11 is provided with the first ultrasound transducer array 311 and the second ultrasound transducer array 321, has the opening in the position where the first and the second ultrasound transducer arrays intersect each other, and has the through hole 314 extending to the opening. Further, the engaging parts that cause the first and the second ultrasound transducer arrays to engage with each other are configured in such a manner that the angle at which the first ultrasound transducer array 311 and the second ultrasound transducer array 321 intersect each other is changeable. As a result, the ultrasound probe 3 according to the present embodiment is able to have the medical device rendered, with certainty, in the two or more ultrasound images obtained by performing the scanning processes at the arbitrary angles. Thus, the ultrasound probe 3 makes it possible to improve the efficiency of the manipulation involved in the diagnosis and/or the medical treatment.

Further, according to the present embodiment, the engaging parts are configured with the gear-like engaging part with projections 312 and the gear-like engaging part with recesses 322. The engaging part with projections 312 and the engaging part with recesses 322 are disposed on the central axes of the first ultrasound transducer array 311 and the second ultrasound transducer array 321, respectively. The angle at which the first ultrasound transducer array 311 and the second ultrasound transducer array 321 intersect each other is changed as a result of the engaging parts being driven while the gear-like engaging part with projections 312 and the gear-like engaging part with recesses 322 are engaged with each other. With this arrangement, the ultrasound probe 3 according to the present embodiment is configured as an ultrasound probe with the simple design that is capable of performing the scanning processes on the two axes at the arbitrary angles.

Further, according to the present embodiment, the engaging parts (the engaging part with projections 312 and the engaging part with recesses 322) are driven in such a manner that either the first ultrasound transducer array 311 or the second ultrasound transducer array 321 scans such a cross-sectional plane that minimizes the distance between the puncture target region and the blood vessel. With this arrangement, the ultrasound probe 3 according to the present embodiment is able to cause the shortest distance to the blood vessel to be displayed and is able to prevent the blood vessel from being damaged during the puncture process.

Further, according to the present embodiment, the engaging parts (the engaging part with projections 312 and the engaging part with recesses 322) are driven in such a manner that either the first ultrasound transducer array 311 or the second ultrasound transducer array 321 scans such a cross-sectional plane that maximizes the length of the puncture target region. With this arrangement, the ultrasound probe 3 according to the present embodiment is able to cause such a cross-sectional plane that maximizes the length of the puncture target region to be displayed and makes it possible to cauterize the puncture target region without excess or insufficiency.

Further, according to the present embodiment, the ultrasound probe 3 receives, through the first ultrasound transducer array 311 and the second ultrasound transducer array 321, the reflected-wave signals used for displaying the first cross-sectional image, the second cross-sectional image, and the three-dimensional image at the same time on the predetermined display unit. With this arrangement, the ultrasound probe 3 according to the present embodiment is able to cause the first cross-sectional image, the second cross-sectional image, and the three-dimensional image to be displayed at the same time on the predetermined display unit and thus makes it possible to improve the efficiency of the diagnosis and the precision level of the diagnosis.

Further, according to the present embodiment, the first ultrasound transducer array 13$a$ and the second ultrasound transducer array 13$b$ are configured in such a manner that the angle at which these ultrasound transducer arrays intersect each other is changeable. With this arrangement, the ultrasound probe 1 according to the present embodiment is able to generate the images at various angles depending on the image capturing target and thus makes it possible to improve the efficiency of the manipulation involved in the diagnosis and/or the medical treatment.

Further, according to the present embodiment, the first ultrasound transducer array 13$a$ and the second ultrasound transducer array 13$b$ are configured to be separatable from each other and are each configured to function as an independent ultrasound transducer while being in the separated state. With this arrangement, the ultrasound probe 1 according to the present embodiment makes it possible to perform various manipulations using the two ultrasound probes.

Further, according to the present embodiment, the probe main body 11 determines the advancing direction of the medical device that advances out of the opening 14$b$ via the through hole. With this arrangement, the ultrasound probe 1 according to the present embodiment makes it possible to position the medical device perpendicular to the ultrasound transducer arrays, with certainty.

Further, according to the present embodiment, the ultrasound probe is provided with the vibration mechanism configured to cause the medical device inserted in the through hole to vibrate in the directions along the through hole. With this arrangement, the ultrasound probe 1 according to the present embodiment makes it possible to perform flexible puncture operations.

Further, according to the present embodiment, the probe main body 11 is configured so that the medical fluid flows through the through hole and flows out of the opening 14$b$. With this arrangement, the ultrasound probe 1 according to the present embodiment makes it possible to improve the efficiency of the manipulation involved in the diagnosis and/or the medical treatment.

As explained above, according to the exemplary embodiments, the ultrasound probe and the ultrasound diagnosis apparatus according to an aspect make it possible to improve the manipulation involved in the diagnosis and/or the medical treatment.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound probe comprising:
a first ultrasound transducer array used for scanning a first scanned plane;
a second ultrasound transducer array that is configured to engage with the first ultrasound transducer array, is provided so as to intersect the first ultrasound transducer array, and is used for scanning a second scanned plane different from the first scanned plane;
gears configured to engage the first ultrasound transducer array and the second ultrasound transducer array; and
a probe main body that is provided with the first ultrasound transducer array and the second ultrasound transducer array, has an opening in a position where the first and the second ultrasound transducer arrays intersect each other, and has a through hole extending to the opening, wherein
the gears include a first gear with projections and a second gear with recesses,
the first gear with projections and the second gear with recesses are disposed on central axes of the first ultrasound transducer array and the second ultrasound transducer array, respectively, and
an angle at which the first and the second ultrasound transducer arrays intersect each other is changed as a result of the gears being driven while the first gear with projections and the second gear with recesses are engaged with each other.

2. The ultrasound probe according to claim 1, wherein the first and the second ultrasound transducer arrays are configured to separate from each other and are each configured to be used as an independent ultrasound transducer while being in a separated state.

3. The ultrasound probe according to claim 1, wherein the gears are configured to drive in such a manner that one of the first and the second ultrasound transducer arrays scans such a cross-sectional plane that minimizes a distance between a puncture target region and a blood vessel.

4. The ultrasound probe according to claim 1, wherein the gears are configured to drive in such a manner that one of the first and the second ultrasound transducer arrays scans such a cross-sectional plane that maximizes a length of a puncture target region.

5. The ultrasound probe according to claim 1, wherein the through hole is formed so as to limit an advancing direction of a medical device that advances out of the opening via the through hole.

6. The ultrasound probe according to claim 5, further comprising: a vibrator configured to cause the medical device inserted in the through hole to vibrate in directions along the through hole.

7. The ultrasound probe according to claim 1, wherein the probe main body is configured to flow medical fluid through the through hole and flow out the medical fluid via the opening.

8. The ultrasound probe according to claim 1, wherein the probe main body is configured to receive, through the first ultrasound transducer array and the second ultrasound transducer array, reflected-wave signals used for displaying a first cross-sectional image, a second cross-sectional image, and a three-dimensional image at a same time on a predetermined display.

9. An ultrasound diagnosis apparatus comprising:
an ultrasound probe that includes:
  a first ultrasound transducer array used for scanning a first scanned plane;
  a second ultrasound transducer array that is configured to engage with the first ultrasound transducer array, is provided so as to intersect the first ultrasound transducer array, and is used for scanning a second scanned plane different from the first scanned plane;
  gears configured to engage the first ultrasound transducer array and the second ultrasound transducer array; and
  a probe main body that is provided with the first ultrasound transducer array and the second ultrasound transducer array, has an opening in a position where the first and the second ultrasound transducer arrays intersect each other, and has a through hole extending to the opening; and
processing circuitry configured to
  generate an ultrasound image based on a reflected-wave signal received by the ultrasound probe, and
  cause a predetermined display to display the ultrasound image generated, wherein
the gears include a first gear with projections and a second gear with recesses,
the first gear with projections and the second gear with recesses are disposed on central axes of the first ultrasound transducer array and the second ultrasound transducer array, respectively, and
an angle at which the first and the second ultrasound transducer arrays intersect each other is changed as a result of the gears being driven while the first gear with projections and the second gear with recesses are engaged with each other.

10. The ultrasound diagnosis apparatus according to claim 9, wherein the first and the second ultrasound transducer arrays are configured to separate from each other and are each configured to be used as an independent ultrasound transducer while being in a separated state.

11. The ultrasound diagnosis apparatus according to claim 9, wherein the gears are configured to drive in such a manner that one of the first and the second ultrasound transducer arrays scans such a cross-sectional plane that minimizes a distance between a puncture target region and a blood vessel.

12. The ultrasound diagnosis apparatus according to claim 9, wherein the gears are configured to drive in such a manner that one of the first and the second ultrasound transducer arrays scans such a cross-sectional plane that maximizes a length of a puncture target region.

13. The ultrasound diagnosis apparatus according to claim 9, wherein the through hole is formed so as to limit an advancing direction of a medical device that advances out of the opening via the through hole.

14. The ultrasound diagnosis apparatus according to claim 13, further comprising: a vibrator configured to cause the medical device inserted in the through hole to vibrate in directions along the through hole.

15. The ultrasound diagnosis apparatus according to claim 9, wherein the probe main body is configured to flow medical fluid through the through hole and flow out the medical fluid via the opening.

16. The ultrasound diagnosis apparatus according to claim 9, wherein
the probe main body is configured to receive, through the first ultrasound transducer array and the second ultrasound transducer array, reflected-wave signals used for displaying a first cross-sectional image, a second cross-sectional image, and a three-dimensional image at a same time on the predetermined display, and
the processing circuitry is configured to
  generate the first cross-sectional image, the second cross-sectional image, and the three-dimensional image, based on the reflected-wave signals received by the probe main body, and
  cause the predetermined display to display the first cross-sectional image, the second cross-sectional image, and the three-dimensional image at the same time.

* * * * *